(12) United States Patent
Lennertz et al.

(10) Patent No.: US 10,842,582 B2
(45) Date of Patent: Nov. 24, 2020

(54) STERILE SURGICAL DRAPE WITH INHERENTLY STABLE TRACKING REFERENCE ARRAY COVER

(71) Applicant: Brainlab AG, Munich (DE)

(72) Inventors: Philippe Lennertz, Munich (DE); Markus Conrad, Munich (DE); Norman Plassky, Munich (DE); Robert Schmidt, Neubiberg (DE)

(73) Assignee: Brainlab AG, Munich (DE)

( * ) Notice: Subject to any disclaimer, the term of this patent is extended or adjusted under 35 U.S.C. 154(b) by 713 days.

(21) Appl. No.: 15/521,679

(22) PCT Filed: Feb. 26, 2016

(86) PCT No.: PCT/EP2016/054098
§ 371 (c)(1),
(2) Date: Apr. 25, 2017

(87) PCT Pub. No.: WO2017/144115
PCT Pub. Date: Aug. 31, 2017

(65) Prior Publication Data
US 2018/0116746 A1    May 3, 2018

(51) Int. Cl.
*A61B 46/10*  (2016.01)
*A61B 34/20*  (2016.01)
*A61B 46/23*  (2016.01)
*A61B 90/00*  (2016.01)
*A61B 90/96*  (2016.01)
*A61B 46/00*  (2016.01)

(52) U.S. Cl.
CPC .............. *A61B 46/10* (2016.02); *A61B 34/20* (2016.02); *A61B 46/23* (2016.02); *A61B 46/40* (2016.02); *A61B 90/96* (2016.02); *A61B 2034/2055* (2016.02); *A61B 2090/3983* (2016.02)

(58) Field of Classification Search
CPC ......... A61B 46/10; A61B 46/23; A61B 34/20; A61B 90/96; A61B 2034/2055; A61B 46/40; A61B 2090/3983
USPC ......................................................... 128/852
See application file for complete search history.

(56) References Cited

U.S. PATENT DOCUMENTS

| 7,688,998 B2 | 3/2010 | Tuma et al. |
| 8,844,538 B2 | 9/2014 | Stang |
| 2006/0140464 A1 | 6/2006 | Feilkas et al. |

(Continued)

FOREIGN PATENT DOCUMENTS

| DE | 10 2010 036 719 A1 | 2/2012 |
| EP | 1 563 799 A1 | 8/2005 |

(Continued)

OTHER PUBLICATIONS

European Patent Office, International Search Report and Written Opinion for corresponding PCT/EP2016/054098, dated Nov. 10, 2016, pp. 1-11.

*Primary Examiner* — Tarla R Patel
(74) *Attorney, Agent, or Firm* — Tucker Ellis LLP

(57) ABSTRACT

The invention relates to a sterile surgical drape comprising a cover portion for a tracking reference array, wherein at least a part of the cover portion is formed inherently stable and has a form adapted to accommodate multiple tracking markers of a tracking reference array for computer-assisted surgery. Further, it relates to a surgical draping system and a medical navigation method using such a drape.

15 Claims, 4 Drawing Sheets

(56) References Cited

U.S. PATENT DOCUMENTS

| | | |
|---|---|---|
| 2007/0175486 A1 | 8/2007 | Bogojevic et al. |
| 2011/0286098 A1 | 11/2011 | Hauri et al. |
| 2012/0305650 A1* | 12/2012 | Prpa .................. G06K 7/10821 235/470 |
| 2014/0261456 A1* | 9/2014 | Malackowski ...... A61B 90/361 128/849 |
| 2014/0318551 A1 | 10/2014 | Daly |

FOREIGN PATENT DOCUMENTS

| | | |
|---|---|---|
| EP | 1 810 636 A1 | 7/2007 |
| WO | 2011038792 A1 | 4/2011 |

* cited by examiner

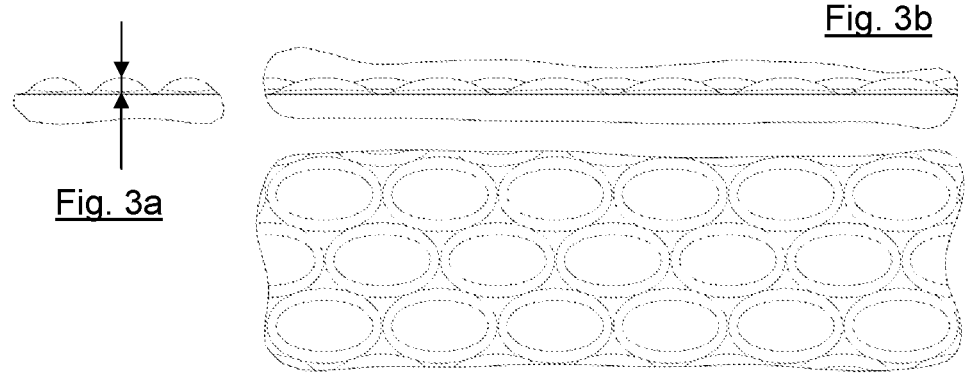
Fig. 3a  Fig. 3b
Fig. 3c
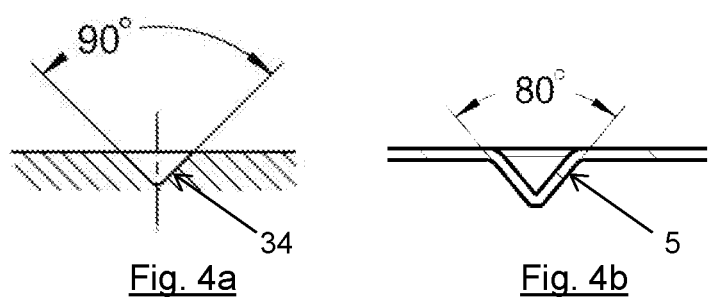
Fig. 4a  Fig. 4b
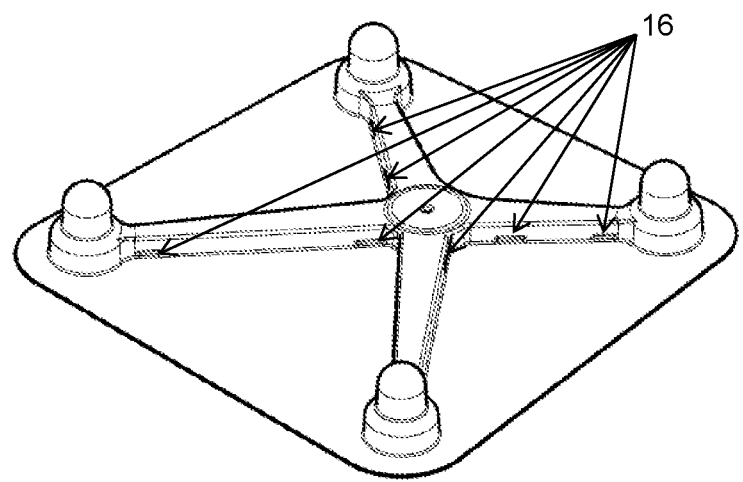
Fig. 5

STERILE SURGICAL DRAPE WITH INHERENTLY STABLE TRACKING REFERENCE ARRAY COVER

RELATED APPLICATION DATA

This application is a national phase application of International Application No.: PCT/EP2016/064098 filed on Feb. 26, 2016.

TECHNICAL FIELD

The present invention relates to a sterile surgical drape, a surgical draping system and a medical navigation method using such a drape.

Sterile surgical drapes are used to cover patients or medical instruments in operating rooms in order to keep the environment of the operation site sterile. EP 1 810 636 A1 describes a sterile drape including a flat film portion for covering C-arm attachments. DE 10 2010 036 719 A1 suggests to use a cladding layer completely surrounding a retro-reflective ball marker of a passive tracker system for optical medical navigation. Shells or casings for tracking markers are disclosed in US 2006/140464 A1 and US 2011/286098 A1.

SUMMARY

According to a general aspect of the invention, a sterile surgical drape comprises a cover portion for a tracking reference array, wherein at least a part of the cover portion is formed inherently stable and has a form adapted to accommodate multiple tracking markers of a tracking reference array for computer-assisted surgery.

In this manner, it is possible to drape the entire tracking reference array and its plurality of tracking markers together with the other areas to be draped in one main draping step and still have access to and information about important bodily and functional features of the array, for example its location and orientation or its functional navigation and tracking features. Separate draping work or draping utilities for keeping the tracking reference array out of the sterile field are rendered unnecessary. Moreover, the installation and calibration of new, additional tracking devices after the draping procedure can be dispensed with which saves time and preserves the original precision of the navigation.

In order to provide the inherent stability, the cover portion can be made of a rigid plastic material, for example a PETG material (polyethylene terephthalate glycol-modified), which has been formed or thermoformed to fit the contour of the tracking reference array, for example formed as a blister cover. In this manner, very thin yet stable cover portions can be achieved so the original features of the tracking array can well be accessed after draping.

The cover portion can be adapted to cover the upper portion of the entire tracking reference array. By "upper portion", usually the portion typically facing a camera setup of an installed tracking system is meant. The tracking reference array can have a predetermined or standard form or a form which is adapted to and in many cases used in the operation carried out. In an exemplary embodiment, it comprises a tracking marker carrier structure and active or passive tracking markers.

In an embodiment of the sterile surgical drape, at least a part of the cover portion is transparent, for example the part covering tracking markers on the tracking reference array. As mentioned above, the access to a bodily representation of the reference array by the provision of the form-adapted cover portion can already provide very helpful information in a fully draped state. This is because, for example, landmarks on the cover can be accessed for navigational or tracking purposes and orientation information is available. If, in addition, transparency is provided for in certain regions or all over the cover, line-of-sight information can be accessed which, in case of the transparent marker cover portions, means that the optical tracking can be continued after the draping procedure.

The cover portion can be provided with transparent clear areas which are highly light-permeable or have high optical properties, for example surface roughness values Rz in the range of 1 to 3, for example 1. Microscope compatibility for verification or calibration purposes can be achieved by integrating such areas with high optical properties (~Rz 1, no particle or air enclosures) in the rigid transparent cover at defined positions to create microscope access to certain locations on the tracking reference array.

According to an embodiment, the cover portion has areas with minimized retro-reflection characteristics, which areas have a surface or surface structure avoiding reflections, for example

- a macro scale structure comprising indentations, protrusions or dimples, and/or
- a micro scale structure created by a surface treatment such as a blasting method, for example creating surface roughness values Rz in the range of 14 to 18, for example 16, and/or
- a painting with retro-reflection-minimizing color on the surface, and/or
- an adhesive material with desired minimal retro-reflection.

Reflections on the cover portion can lead to tracking issues with an optical tracking system. For example, the infrared light emitted from the navigation system's camera setup gets reflected at flat or even surfaces. For flat surfaces which are perpendicular to the camera's line of sight, the reflected light gets recognized by the camera and might lead to an unwanted additional marker being created in the navigation software procedure or a high deviation of the calculated center of a retro-reflective marker sphere compared to its actual spatial position. Those problems and, in particular additional markers, can be avoided by the above measures.

On a macro scale, a dimpled surface similar to a golf ball could be named as example. The structure's elevation could be approximately 1 mm and the fraction of flat, non-curved surface as small as possible. By adding a macro scale structure to the rigid transparent cover's surface, the (infrared) light emitted by the navigation system or operating room lights is reflected into multiple directions. The angle of incidence of light rays is changing continuously and therefore the angle of the reflected light also changes continuously along the rigid transparent cover's surface and parallel light rays get scattered by the reflection on such a structured surface which can still maintain its transparence.

A micro scale structure can for instance be generated by glass bead blasting the cover's surface (~Rz 16) in those areas where reflections are to be controlled. On a micro scale, the same effect as described with the macro scale structure is used, but only with a way smaller structure. The reflections are scattered into many directions due to different angles of incidence of the light rays. Compared to the macro scale solution the surface of the rigid cover is more opaque.

On the surface of the cover portion, calibration recesses or reference points, for example recessed, engraved or printed recesses or points, can be formed at positions which mirror or correspond to the position of respective recesses or points on the tracking reference array, in order to provide separate calibration or reference locations associated to the respective drape. For example, for the purpose of instrument calibration/verification with the cover applied, a conical recess can be formed on the cover's surface at a location right above a conical instrument calibration/verification recess of the tracking reference array.

If, in such a way, the calibration/verification recess of the tracking reference array is also formed into the rigid cover, instrument tips such as pointer tips can be placed in this cover recess and verified or calibrated, though at a slightly deviated position compared to the original navigation tracker's recess. By using a thin (~0.5 mm) PETG foil as stiff cover material and by specifying an angle of ~80° for the cover's recess instead of 90° of the original array's recess, this deviation can be kept very low (close to the foil thickness of ~0.5 mm). The smaller angle of the recess avoids unwanted collision of the rigid cover—which needs a radius at the recesses edge due to the thermoforming process—with the edge of the navigation tracking array's recess.

One embodiment envisages marking or designating, on the surface of the cover portion, one or more additional functional areas, such as
- retro-reflective tracking markers, for example flat markers,
- device identification labels, for example UDI (Unique Device Identification) labels,
- remote control areas, for example on defined areas of the cover portion, or labels such as symbols, text markers or color codes, recognizable for a medical navigation system and creating commands when interacting with a navigated instrument.

Such a marking or designating of functional areas may have multiple purposes and advantages. For example, in order to recognize the presence of the cover on a tracking reference array (or "navigation tracker"), an additional reflective marker (e.g. flat marker) can be added to the rigid cover. Alternatively, a UDI label (barcode, QR code, etc.) can be added to the cover if this kind of additional information is made recognizable to the navigation system used. If the presence is known, certain deviations and differences, such as new positions, can be compensated by the navigation system. In another alternative, new reference points (printed, engraved, laser labeled etc.) could be added onto/into the cover for microscope verification/user calibration.

Remote control functionality can be achieved by recognizing whether the position of an instrument tip such as a tracked pointer tip is within a defined spatial area. By means of the tracking and navigation system, it is determined whether the tip is held on the cover's surface and onto one especially marked or designated area or location, for example inside one quadrant of the rectangle spanned by the four marker spheres. Further, the cover's surface can be labeled with symbols and color coded to visualize the presence of remote control areas to the user. The provision of navigation functionality will allow for a sterile use of the navigation system without having to drape the (touch) screen in use. One more detailed example: A navigation system continuously tracks the position of an instrument tip. If this position matches a defined area on the cover's surface, it can be assumed that the user wants to remotely control the navigation system. The navigation system could then perform certain actions like going to the next or previous navigation page. A user would, thus, not have to operate the unsterile touch screen. Especially in cases where the sterile surgeon needs to operate the navigation system without draping it, this feature is beneficial, but also if the touchscreen of the navigation system is placed too far away for the user to reach it, for instance.

For microscope verification or user calibration, respectively, new positions can also be recognized by means of cover markers or labels and loaded into and taken into account by the navigation system. On the other hand, the user can focus the optics either on labeled, for instance laser labeled, landmarks or on the ground of the calibration/verification recess which can be formed as a central recess on the reference array. By integrating areas with high optical properties (~Rz 1, no particle or air enclosure) into the cover, it is possible to see and focus through the cover material without significant deviations of the light rays. This makes it possible to focus the optics on existing labeled landmarks underneath the transparent cover, e.g. on the bottom of the tracking reference array's central recess. Alternatively new landmarks can be added onto/into the rigid transparent cover and the user could focus on these instead without having to focus through the rigid transparent cover.

The drape can comprise a flexible outer drape portion or sterility barrier, for example of fabric or foil material, joining or encompassing the cover portion at a joining area, for example a seam. In such an embodiment, it is possible to adapt the drape such that it can be folded into a pack having an orientation guide visible on one side and showing the orientation of the cover portion of the drape to the user. For example, the array-accommodating side of the cover portion rests on the lower side of the pack, whereas, on the upper side of the pack, the orientation of the cover portion is labeled or printed by means of a symbol or a symbolic representation of the cover portion. Both, the cover and the reference array can, for instance, be labeled with an identical shape (e.g. a triangle) to help the user find the right orientation to mount the cover correctly onto the array. This will help the user to install the drape correctly on the first try and, therefore, save time.

On its lower surface, the cover portion can be provided with one or more holders to engage with the tracking reference array in order to fasten the cover portion thereon, for example undercuts for engaging a lower edge or rim of the tracking reference array. This will fasten the cover securely on the array, though the cover will still be detachable because of its elastic material properties.

In accordance with a further aspect of the invention, a surgical draping system comprises at least two layers of sterile surgical drapes in accordance with one or more of the embodiments discussed above, wherein an overlying cover portion of one drape is adapted to snugly accommodate an underlying cover portion of another drape. The stability of the cover portion provides for such a stacking capability which offers multiple advantages. For example, in a case where a draped and navigationally registered patient is to be moved from the surgical site to an imaging apparatus for an intra-operative scan, a second drape can be applied which would keep the first drape sterile and the registration in place and would still provide for tracking capability during the scan, namely "through" the two stacked cover portions.

Stacking can be achieved by enlarging the size of the geometry slightly (~0.5 mm) for each additional cover added.

The overlying cover portion can be equipped with an identification marker or label uniquely identifying it or distinguishing it from the underlying cover portion, by positional or symbolic information to be received and processed by a medical navigation system. In other words, recognition of stacking can be achieved by, for example, adding a reflective marker (e.g. flat marker) to each additional rigid transparent cover at a position differing from the reflective marker positions of the previous covers already installed. Alternatively each additional cover can be UDI-labeled (Unique Device Identification). When using UDI labels in any form, the additional information must be recognizable by the navigation system. For all alternatives, the gained information can be used to recognize the presence of each additional cover on the navigation tracker. If the presence is known, certain deviations and differences can be compensated for by the navigation system, e.g. new remote control surfaces can be loaded into the navigation system.

Thus, in another aspect, the invention addresses a medical navigation method in which, in a surgical setup, two stacked cover portions of a surgical drape or drape system as discussed above are covering a tracking reference array, wherein an identification marker or label on the second cover portion is recognized by a medical navigation system, and wherein positional deviations in the navigation caused by known positional shifts of one or more overlying drape features, for example the functional areas or calibration or reference locations, are compensated for by re-calculating and re-calibrating the navigation on the shifted positional basis.

The surgical drape, the surgical draping system and the medical navigation method are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital light-box. The monitor may also be the monitor of a portable, for example handheld, device such as a smart phone or personal digital assistant or digital media player.

Registering

The n-dimensional image of a body is registered when the spatial location of each point of an actual object within a space, for example a body part in an operating theatre, is assigned an image data point of an image (CT, MR, etc.) stored in a navigation system.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Pointer

A pointer is a rod which comprises one or more—advantageously, three—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Reference Array

A reference array refers to a device with a number of markers, advantageously four markers, attached to it, wherein the markers are (for example detachably) attached to the reference array such that they are stationary, thus providing a known (and advantageously fixed) position of the markers relative to each other. The position of the markers relative to each other can be individually different for each reference array used within the framework of a surgical navigation method, in order to enable a surgical navigation system to identify the corresponding reference array on the basis of the position of its markers relative to each other. It is therefore also then possible for the objects (for example, instruments and/or parts of a body) to which the reference array is attached to be identified and/or differentiated accordingly. In a surgical navigation method, the reference array serves to attach a plurality of markers to an object (for example, a bone or a medical instrument) in order to be able to detect the position of the object (i.e. its spatial location and/or alignment). Such a reference array for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Medical/Surgical Navigation System

A navigation system, such as a medical or surgical navigation system, is understood to mean a system which can comprise: at least two marker devices; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body.

The invention does not involve or in particular comprise or encompass any surgical or therapeutic activity. No surgical or therapeutic step is necessitated or implied by carrying out the invention. In particular, the invention does not involve or in particular comprise or encompass an invasive step which would represent a substantial physical interference with the body requiring professional medical expertise to be carried out and entailing a substantial health risk even when carried out with the required professional care and expertise.

BRIEF DESCRIPTION OF DRAWINGS

In the following, the invention is described with reference to the enclosed figures which represent preferred embodiments of the invention. The scope of the invention is not however limited to the specific features disclosed in the figures, in which.

-continued

Figure 6:
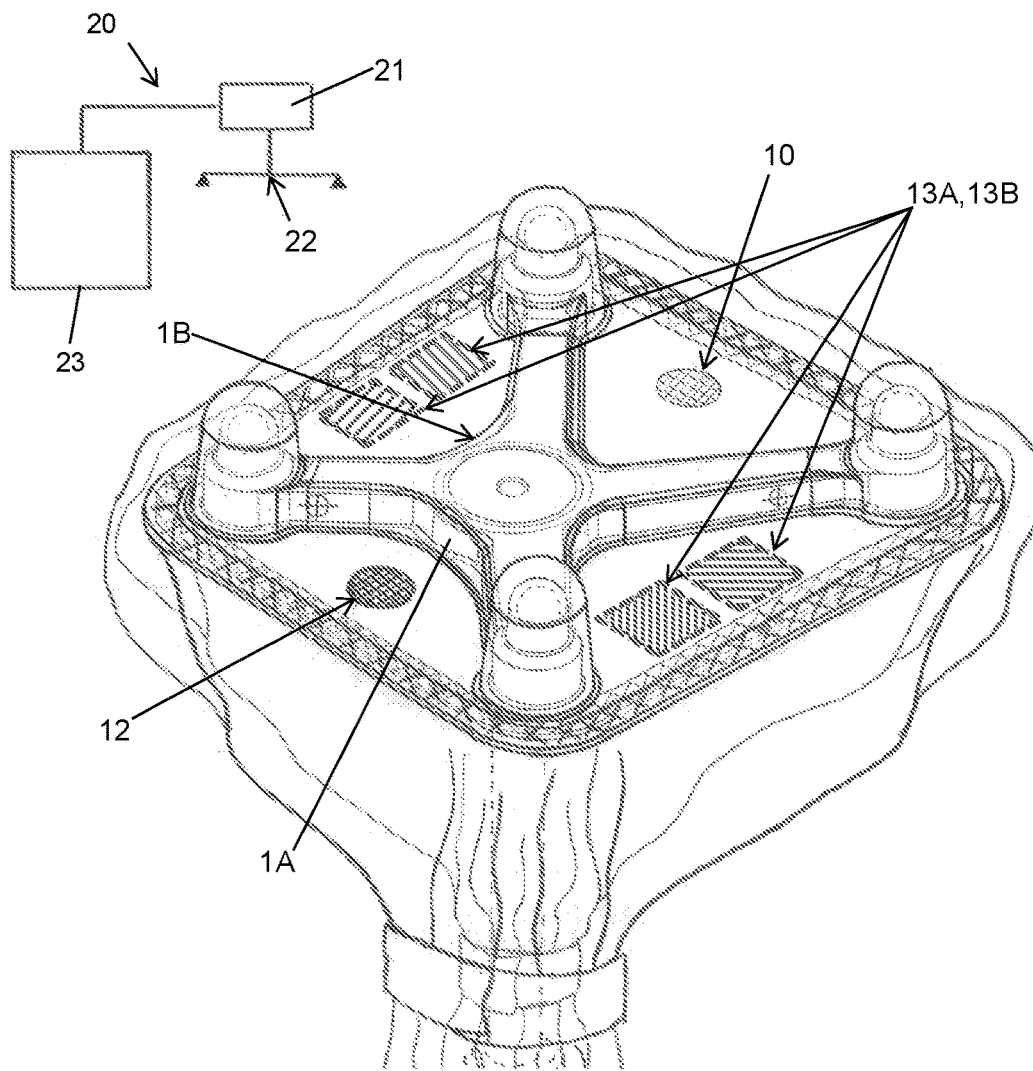
Figure 7A:
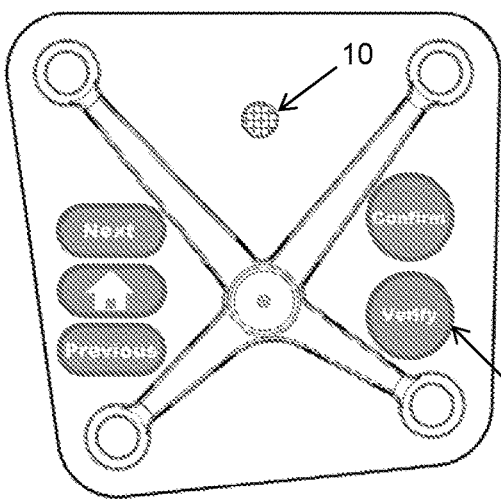
Figure 7B:
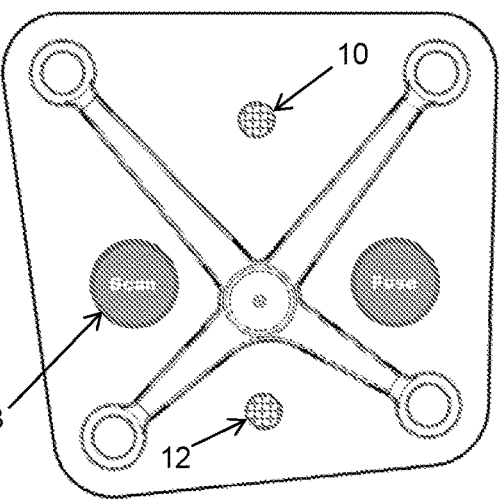
Figure 8:
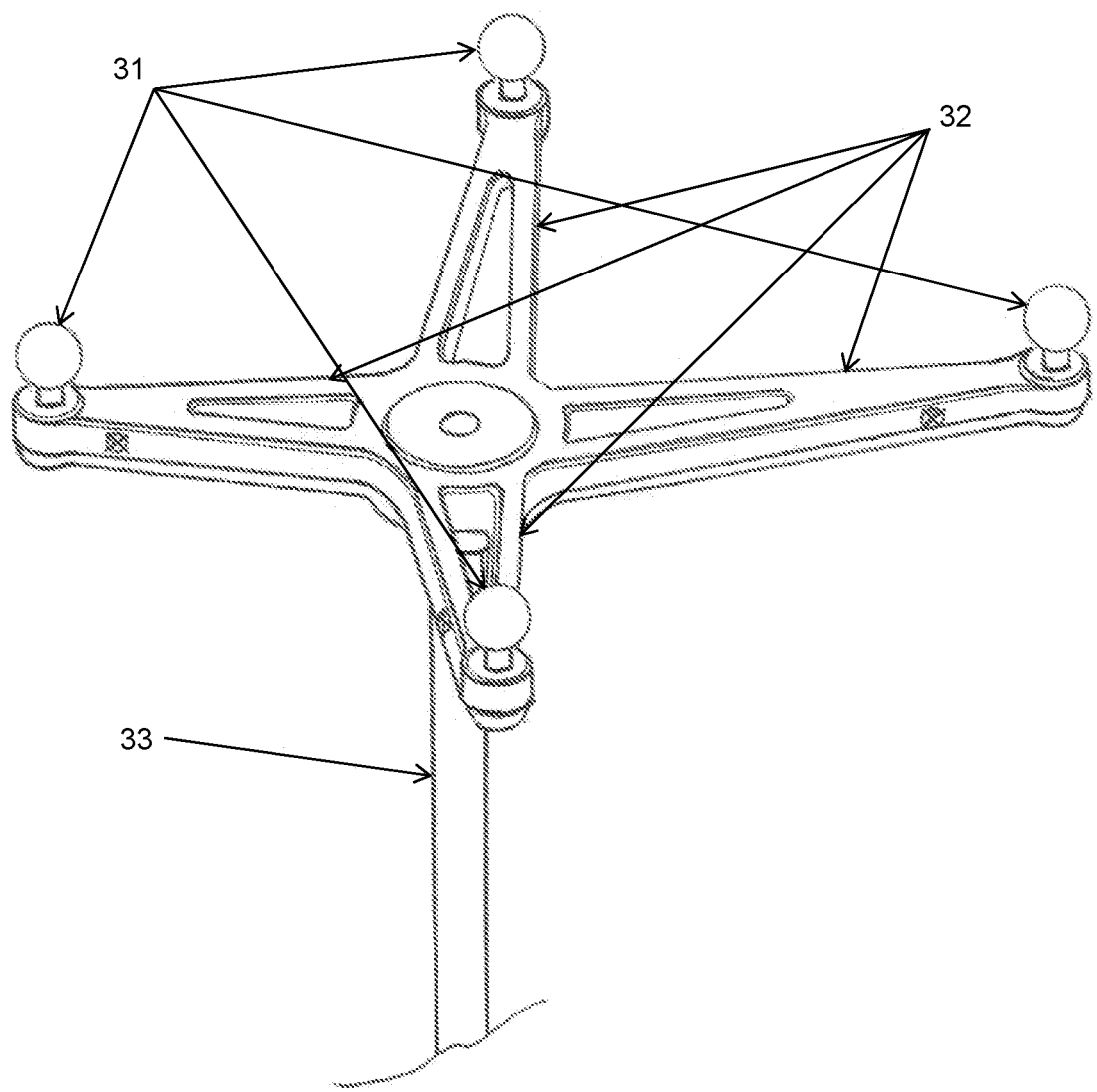

| FIG. 3a, 3b and 3c | show three isometric views of a macro scale surface structure with minimized retro-reflection characteristics; |
|---|---|
| FIGS. 4a and 4b | show the angular geometry of a calibration recess of a tracking reference array and the respective portion of an outer sterile cover; |
| FIG. 5 | shows an embodiment of the cover portion having undercuts for engaging a tracking reference array; |
| FIG. 6 | shows an embodiment having two drapes with stacked cover portions arranged over a reference array and featuring functional markings; |
| FIG. 7a and 7b | are upper views of cover portions with markings having remote control functionality; and |
| FIG. 8 | is a perspective representation of an embodiment of a tracking reference array. |

DETAILED DESCRIPTION

Certain embodiments of the present invention will now be described in detail and with reference to the Figures. The invention is directed to the draping of a tracking reference array and, to begin with, an embodiment of such a tracking reference array will be described referring to FIG. 8. The tracking reference array is, in its entirety, identified by reference numeral 30 and it comprises a holding element 33 connected to the center portion of a four-armed marker holder. At the end of each arm 32, the marker holder has markers 31, in the present case spherical reflection markers. A central recess 34 is formed in the middle portion of the marker holder, serving as a calibration, verification or registration point in which, for example, instrument tips can be positioned for instrument registration/verification purposes or on which a microscope optics can be focused for such purposes. The tracking reference array can, by means of its markers 31, be tracked, followed and navigated in a navigation system equipped with a camera tracking system.

Figure 1:
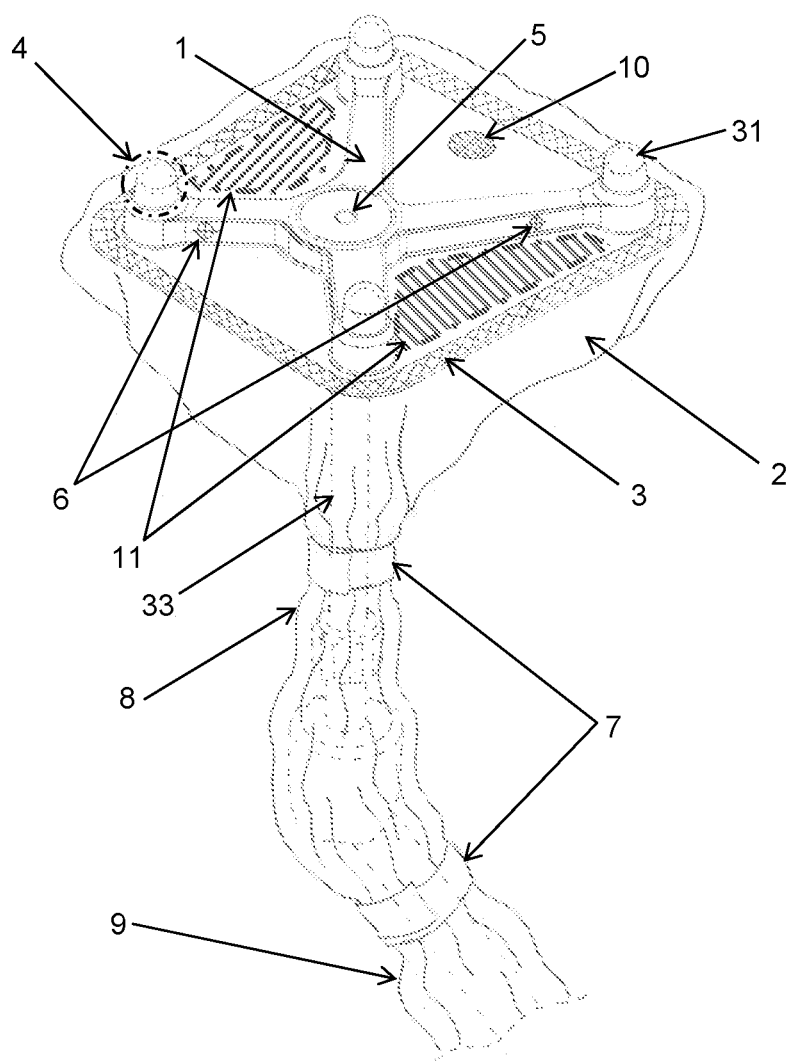
FIG. 1   is a perspective view of an embodiment of a surgical drape placed over a reference array.

A tracking reference array such as the one shown in FIG. 8 can be draped with a sterile surgical drape according to the present invention, and an embodiment thereof is shown in FIG. 1. The drape of FIG. 1 has a cover portion 1 with a stable form, in this embodiment a rigid transparent cover formed as a blister, and a flexible sterile barrier 2, for example of fabric or foil material. The cover portion 1 and the barrier 2 are connected to each other at a defined joining area which is embodied as a scheme 3. The scheme 3 is designed such that it does not impair the sterility of the entire drape, this being for instance achieved by heat sealing, gluing or heat activated gluing. The blister portion 1 is designed to be adapted to and fit on the tracking reference array 30. In FIG. 1 the holding element 33, markers 31 and reference array mounting base are indicated in broken lines. The entire drape is sized to cover the tracking reference array 30 as well as the holding element 33 and parts of the reference array mounting base 35 by covering it with the lower portions 8 and 9 of the barrier 2. For gathering the barrier material in those lower portions 8 and 9, drape fixation tape 7 or similar solutions can be used, such as rubber bands, cords, etc.).

In order to optimize the optical tracking of the reference array by a surgical navigation system, the areas of the rigid transparent cover 1 surrounding the markers 31 of the tracking reference array 30 are designed and formed in such a way that they have high optical properties. Those areas are designated as optically relevant areas with the reference numeral 4. Providing those areas with high optical properties is achieved by defining a small thickness of the transparent material (~0.5 mm) as well as defining a polished (Rz~1) tool surface for thermoforming such optical relevant areas 4. Furthermore, the transparent material in the region of those optically relevant areas is formed such that it does not have any entrapped air or particles which would impair accurate tracking of the markers 31.

In FIG. 1, microscope focusing landmarks on the reference array are designated by reference numeral 6, and those landmarks 6 usually serve as calibration/verification focusing points on the reference array 30. The areas of the blister 1 which match the positions of the landmarks 6 and the central instrument verification recess 34 (blister area 5) will then be optically relevant areas, too. They will have the above-mentioned high optical properties.

As mentioned above, the functionality of the central recess 34 of the tracking reference array 30 is preserved by forming the corresponding recess 5 into the blister material at the respective location. The blister recess 5 is accommodated in the array recess 34 which helps to secure the blister 1 on the array. The material thickness of the blister portion 1 causes a small deviation of the verification/calibration position provided by the original recess 34 of the tracking reference array 30, and in order to keep this deviation as small as possible, the angle of the thermoformed blister recess 5 (see FIG. 4b) shall be smaller (~80°) the angle of the reference array's recess of 90° (see FIG. 4a).

Figure 2:
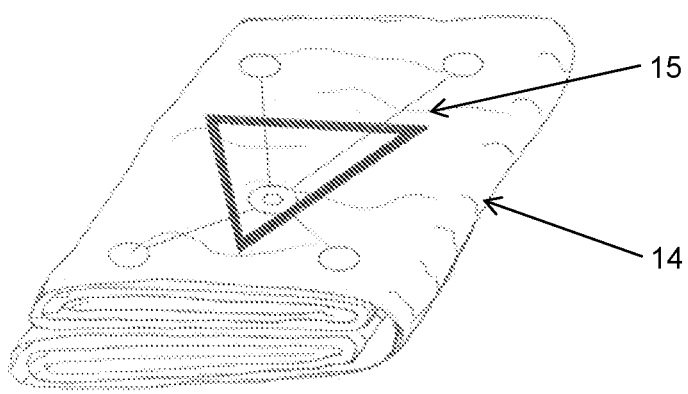
FIG. 2   shows an embodiment of a surgical drape folded into a pack and having an orientation guide on its outer layer.

FIG. 2 shows a pack of folded drape to be positioned over a tracking reference array. The pack 14 has, not visible here, but present on its lower side, a blister portion 1. To be applied correctly, it must be brought down onto the reference array in the correct orientation. To this end, symbols or the geometry of the reference array, here designated as 15, are labeled onto the upper side of the drape pack 14 to help the user to give the drape the correct orientation at the first try. If a symbol is chosen for this purpose, the symbol can also be displayed on the reference array.

Avoiding unwanted reflections on flat surfaces of the blister portion 1 is essential for the unrestricted use of the drape. Otherwise, certain angles of view between a tracking camera setup and the blister portion 1 (angles close to a perpendicular view onto the blister surfaces) will be restricted because reflections will occur which might be detected as unwanted additional markers by a navigation system. If such reflections or additional markers occur close to one of the markers 31 of the reference array, huge accuracy deviations can be caused or an instrument will not be detected at all by the navigation system. To avoid this, micro-scale or macro-scale structures on the blister material may be created, which provide for a continuous change of the surface orientation such that those disadvantageous light reflections do not occur.

An example for a macro-scale structure is shown in the three isometric views of FIGS. 3a, 3b and 3c. This structure has small round protrusions next to each other, wherein the height as shown in FIG. 3a by the arrows shall be approximately 1 mm and the fraction of the remaining flat, non-curved surface stays as small as possible.

Alternatively, a microscale structured surface (e.g. by blasting, Rz~16) can be used to avoid reflections.

In order to hold the cover portion 1 (or blister portion 1) in place on the reference array, it can be provided with undercuts, designated by 16 in FIG. 5. Keeping the blister portion 1 safely in place on the tracking reference array 30 ensures unimpaired visibility of the markers as well as of the microscope landmarks or the central instrument verification recess.

Further functionality can be achieved by marking the blister portion and this will be explained now with reference to FIGS. 6, 7*a* and 7*b*.

In a very general manner, a representation of a navigation system 20 is provided in the upper left corner of FIG. 6. It should be noted that it is, in general, such a navigation system which may be used to provide the tracking navigation functionalities discussed herein in the general description and in the detailed description of the embodiments at the drawings. The navigation system 20 has a camera system 22 which detects light reflected or emitted by navigation markers and the navigation computer 21 translates this information into positional information such that tracked instruments can be displayed in a correct positional relationship to each other or to a registered patient on the screen 23.

By adding an additional marker such as the marker 10 in FIGS. 7*a* and 7*b*, to the surface of the blister 1, it is possible to automatically detect whether a blister portion 1 is present or not. The characteristics of the marker 10 can be made known to the navigation system which will, upon registering such a marker, use the "blister present" information to compensate certain positional deviations or differences introduced by the blister drape or to activate additional functionalities. For example, remote control functionality could be activated, microscope marker positions could be updated or positional deviations of the central instrument verification recess could be compensated.

Remote control of the navigation system is especially beneficial if a sterile user wants to operate the navigation system without impairing his sterility. In FIG. 1, for example, two possible surfaces for remote control functionality are shown and designated by reference numeral 11. By making it known to the navigation system where the remote control surfaces 11 are positioned compared to the marker spheres and by tracking, for example, a pointer tip's position, the navigation system will be able to detect that a pointer tip is being held onto one of the remote control surfaces 11 and a specified action (for example "next page" or "previous page") can be performed by the navigation system. In order to visualize the presence and the functions of remote control surfaces to the user, symbols or interaction fields 13 can be labeled on the blister's surface as is also shown in FIGS. 7*a* and 7*b*.

FIG. 6 shows a situation with two blister portions 1A and 1B where the portion 1B is stacked over portion 1A. Such a situation may occur if a further draping is needed, for example to carry out intra-operative imaging. In FIG. 6 and FIG. 7*b*, an additional marker is designated at 12, and this additional marker 12 communicates to a navigation system that the second, overlaying blister portion 1B is in place. In combination with the markers on the underlying blister portion 1A, a new optically readable code is formed. Alternatively, this information could be coded in a UDI label such as a bar code or a QR-code. When recognizing the second layer blister portion 1B, the navigation system can activate new remote control fields 13 or re-set the original fields 13 of the underlying blister portion 1. Of course, with the knowledge about the presence of the overlaying blister portion, further necessary compensations can be carried out by the navigation system, for instance with the regard to a positional adaptation of the central calibration/verification recess.

The invention claimed is:

1. A sterile surgical drape comprising a cover portion for a tracking reference array having a support structure and a plurality of tracking markers extending from the support structure, wherein at least a part of the cover portion is formed inherently stable such that the part is rigid and has a form adapted to accommodate the support structure and the tracking markers of the tracking reference array for computer-assisted surgery, wherein parts of the cover portion that cover the tracking markers are transparent to allow for tracking of the markers, wherein the cover portion has areas with minimized retro-reflection characteristics that have a surface or surface structure that avoids reflections, and wherein the surface or surface structure includes at least one of a macro scale structure, a micro scale structure, a painting, or an adhesive material.

2. A sterile surgical drape according to claim 1, wherein the cover portion is made of a rigid plastic material formed or thermoformed to fit the contour of the tracking reference array.

3. A sterile surgical drape according to claim 1, wherein the cover portion is adapted to cover the upper portion of the entire tracking reference array.

4. A sterile surgical drape according to claim 1, wherein the parts of the cover portion that cover the tracking markers are transparent clear areas that are highly light-permeable or have high optical properties.

5. A sterile surgical drape according claim 1, wherein:
the macro scale structure comprises indentations, protrusions or dimples, and/or
the micro scale structure is created by a surface treatment, and/or
the painting has retro-reflection-minimizing colour on the surface, and/or
adhesive material has minimal retro-reflection.

6. A sterile surgical drape according to claim 1, wherein, on the surface of the cover portion, calibration recesses or reference points are formed at positions that mirror or correspond to the position of respective recesses or points on the tracking reference array, in order to provide separate calibration or reference locations associated to the sterile surgical drape.

7. A sterile surgical drape according to claim 1, wherein, on the surface of the cover portion, one or more additional functional areas are marked or designated.

8. A sterile surgical drape according to claim 7, wherein the one or more additional functional areas include:
retro-reflective tracking markers;
device identification labels; or
remote control areas or labels in a form of symbols, text markers or colour codes, recognizable for a medical navigation system and creating commands when interacting with a navigated instrument.

9. A sterile surgical drape according to claim 1, further comprising a flexible outer drape portion joining or encompassing the cover portion at a joining area.

10. A sterile surgical drape according claim 9, wherein the sterile surgical drape is adapted to be folded into a pack having an orientation guide visible on one side and showing the orientation of the cover portion of the drape to the user.

11. A sterile surgical drape according to claim 1, wherein the cover portion has a lower surface, and wherein one or more holders are provided on the lower surface to engage with the tracking reference array in order to fasten the cover portion thereon.

12. A surgical draping system comprising at least first and second sterile surgical drapes in accordance with claim 1, wherein an overlying cover portion of the first sterile surgical drape is adapted to snugly accommodate an underlying cover portion of the second sterile surgical drape.

13. A system according to claim 12, wherein the overlying cover portion comprises an identification marker or label uniquely identifying the identification marker or label or distinguishing the identification marker or label from the underlying cover portion, by positional or symbolic information to be received and processed by a medical navigation system.

14. The sterile surgical drape according to claim 1, wherein the support structure includes a plurality of arms, and wherein one of the plurality of tracking markers is at an end of each of the plurality of arms.

15. The sterile surgical drape according to claim 14, wherein the cover portion has a base portion and a raised portion extending upward from the base portion, the raised portion adapted to accommodate the plurality of arms and the tracking markers.

* * * * *